United States Patent [19]
Schmitt et al.

[11] Patent Number: 5,823,778
[45] Date of Patent: Oct. 20, 1998

[54] IMAGING METHOD FOR FABRICATING DENTAL DEVICES

[75] Inventors: Stephen M. Schmitt, San Antonio, Tex.; David A. Chance, Burke, Va.

[73] Assignee: The United States of America as represented by the Secretary of the Air Force, Washington, D.C.

[21] Appl. No.: 871,118

[22] Filed: Jun. 9, 1997

Related U.S. Application Data

[60] Provisional application No. 60/020,523 Jun. 14, 1996.
[51] Int. Cl.⁶ .................................................. A61C 9/00
[52] U.S. Cl. ............................ 433/214; 433/71; 433/223
[58] Field of Search ................................. 433/6, 37, 71, 433/214, 223

[56] References Cited

U.S. PATENT DOCUMENTS

| | | | |
|---|---|---|---|
| 4,742,464 | 5/1988 | Duret et al. | 433/214 X |
| 4,964,770 | 10/1990 | Steinbichler et al. | 433/214 X |
| 5,347,454 | 9/1994 | Mushabac | 433/214 |
| 5,413,481 | 5/1995 | Goppel et al. | 433/214 |
| 5,605,459 | 2/1997 | Kuroda et al. | 433/214 |

OTHER PUBLICATIONS

"Refining Cast Implant–Retained Restorations by Electrical Discharge Machining" Stephen M. Schmiett et al., Journal of Prosthetic Dentistry, vol. 73 No. 3 Mar. 1995 pp. 280–283.

"Fabrication of Titanium Implant—Retained Restoration with Nontraditional Machining Techniques", Stephen M. Schmitt et al., International Journal of Prosthodontics, vol. 8, No. 4, 1995, pp. 323–336.

"Analytical Model Surgery", William H. Bell, Ed, Part 7, Modern Practice In Orthognathic and Reconstructive Surgery, vo. 1.

Primary Examiner—Nicholas D. Lucchesi
Attorney, Agent, or Firm—Bobby D. Scearce; Thomas L. Kundert

[57] ABSTRACT

A method for fabricating a dental restoration is described which comprises the steps of obtaining a dental impression of a patient using dental impression material, filling the cavity defining the impression with a filler material distinguishable from the dental material defining the impression and allowing the materials to harden to a solid block, successively removing from the block thin layers and imaging each then remaining surface of the block after each successive layer is removed to define a contour of the filler material for each layer removed, each contour corresponding to a contour of the teeth, gums and palate of the patient at a corresponding known depth of the block, generating a three dimensional computer model of the teeth, gums and palate of the patient using the contours, and converting the model to a stereolithography file for producing a castable pattern of the model or machining a restoration corresponding to the model.

13 Claims, 5 Drawing Sheets

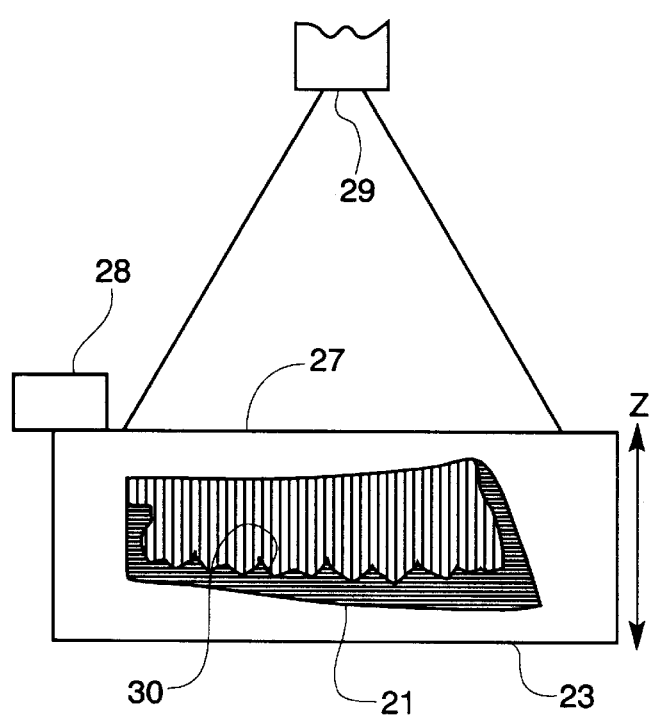
Fig. 6
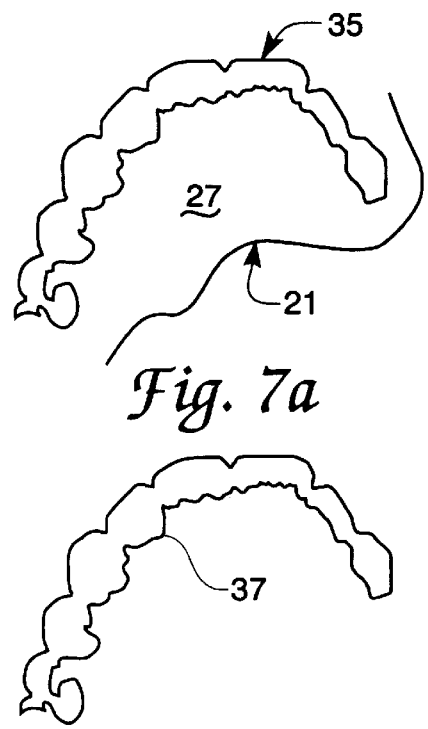
Fig. 7a
Fig. 7b
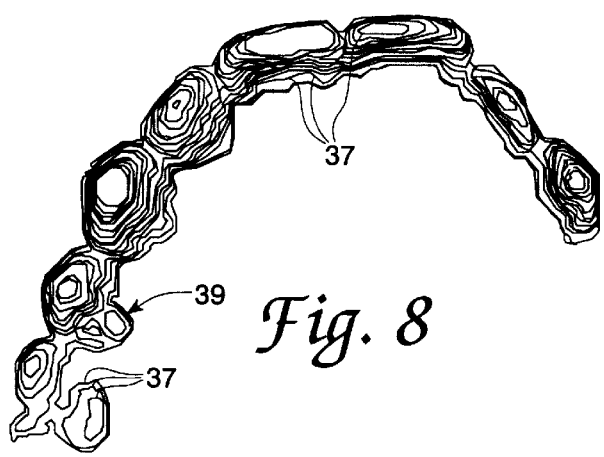
Fig. 8
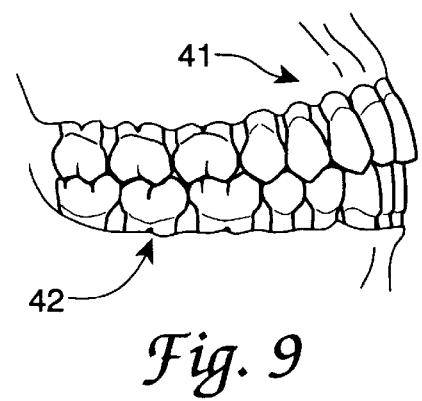
Fig. 9

IMAGING METHOD FOR FABRICATING DENTAL DEVICES

RIGHTS OF THE GOVERNMENT

The invention described herein may be manufactured and used by or for the Government of the United States for all governmental purposes without the payment of any royalty.

This application is a continuation of provisional application Ser. No. 60/020,523, filed Jun. 14, 1996.

BACKGROUND OF THE INVENTION

The present invention relates generally to methods for fabrication of dental restorations and the like, and more particularly to a method for imaging small objects in the custom fabrication of machined dental devices.

Modern manufacturing processes related to large item fabrication have become substantially computer controlled, but the corresponding processes for fabricating small items remain inadequate because of the expense and complexity of acquiring useful digital information on small objects. For example, laser scanning produces a set of data points defining an object by triangulation, the laser beam being projected onto the object and reflected toward a camera; this system requires complex mathematical computations, has problems with objects having shadowed or recessed areas, and requires expensive holding devices for proper orientation of the object. An extension of the laser scanning process uses multiple lines or patterns to cover the object with light, such as the Moiré contouring process, to produce surface data similar to a topographic map; this process cannot effectively distinguish a peak from a valley and requires a large amount of data. The stereo machine vision process obtains parallax views of the object from two different perspectives, but depends on surface features to the extent that smooth featureless surfaces can not be contoured directly. Laser radar operates by illuminating the object with a laser beam and recording the time to sense the return signal, and typically has insufficient resolution for small object imaging. A contact digitizer utilizes a probe contacting the surface of the object to record its contour, but requires a small diameter probe to avoid errors and is a time-consuming process; the probe may bend upon contact with the surface which generates errors and may be ineffective on steep surface contours.

Magnetic Resonance Imaging (MRI) and Computer Tomography (CT) are two imaging techniques commonly used in dentistry and medicine to provide patient diagnostic information. CT is used to image dental and medical patients prior to oral and maxillofacial surgery to correct skeletal dysplasias or to plan for placement of dental implants for missing teeth. However, dental restorations (fillings) produce scatter of radiation used in applying CT and may produce images of the teeth that are non-diagnostic. The precision of CT image data is generally unacceptable for construction of dental devices and restorations. Three dimensional information about dental anatomy is typically obtained using impression materials and dental stone (form of Plaster of Paris), which is an accurate process but requires mechanical mixing, pouring, trimming, cutting, shaping and other highly labor intensive steps to produce a dental restoration.

The present invention solves or substantially reduces in critical importance problems with prior art process as just described by providing a method of imaging small (about 60×60 mm) dental and medical objects and using the resulting digital data to fabricate custom dental devices with minimal manual labor. The invention combines small object imaging, computer aided design (CAD), computer aided manufacturing (CAM), rapid prototyping, computer number controlled (CNC) milling and electrical discharge machining (EDM) to fabricate the desired product. The invention may use conventional dental materials in the computerized acquisition of precise micron level three-dimensional data about a patient's teeth or soft tissues, unaffected by dental restorations and radiographic scatter. The data may be combined with CT data of osseous tissues to produce precise three dimensional computer models of a patient and this information can be used for diagnosis or device manufacture using conventional rapid-prototyping processes. The resulting digital data may be conveniently stored, duplicated and transmitted electronically, which provides a distinct advantage over the present practice of recording three dimensional data about a patient's dental anatomy through impressions and stone dental casts. Labor intensive preparation of casts and the environmental problems associated with preparation, processing and disposal of the casts are avoided. The invention finds substantial utility by dentists, physicians, dental laboratories and the like needing to image small objects precisely. Use of modern fabrication processes such as numerical controlled milling, stereolithography, selective laser sintering, laminated object manufacturing, fused deposition modeling, three dimensional printing and others are facilitated using the digital data generated in the practice of the invention.

It is, therefore, a principal object of the invention to provide a method for fabricating dental restorations.

It is yet another object of the invention to provide a method for preparing a computer model for a dental impression of a patient which may be utilized in precision machining operations for fabricating a dental restoration.

It is yet another object of the invention to combine small object imaging, CAD, CAM, rapid prototyping, CNC milling and EDM to fabricate a precise dental restoration.

It is a further object of the invention to provide a method for fabricating dental restorations defined by data which may be stored or transmitted electronically.

These and other object of the invention will become apparent as a detailed description of the invention proceeds.

SUMMARY OF THE INVENTION

In accordance with the foregoing principles and objects of the invention, a method for fabricating a dental restoration is described which comprises the steps of obtaining a dental impression of a patient using dental impression material, filling the cavity defining the impression with a filler material distinguishable from the dental material defining the impression and allowing the materials to harden to a solid block, successively removing from the block thin layers and imaging each then remaining surface of the block after each successive layer is removed to define a contour of the filler material for each layer removed, each contour corresponding to a contour of the teeth, gums and palate of the patient at a corresponding known depth of the block, generating a three dimensional computer model of the teeth, gums and palate of the patient using the contours, and converting the model to a stereolithography file for producing a castable pattern of the model or machining a restoration corresponding to the model.

BRIEF DESCRIPTION OF THE DRAWINGS

The invention will be more clearly understood from the following detailed description of representative embodiments thereof read in conjunction with the accompanying drawings wherein:

FIG. 6 illustrates the acquisition of an image of the microtome of FIGS. 4 and 5;

FIG. 7a shows a typical image taken according to FIG. 6;

FIG. 7b shows the contour or outline of the image of FIG. 7a;

FIG. 8 is a two dimensional display of a series of contours of FIG. 7b;

FIGS. 9–12 illustrate the acquisition of a triple-tray impression of the upper and lower teeth of a patient and the formation of a microtome block for slicing and imaging similarly to the process illustrated in FIGS. 4–6;

DETAILED DESCRIPTION OF THE INVENTION

Technology related to the invention may be found by reference to articles entitled "Refining Cast Implant-Retained Restorations By Electrical Discharge Machining," by Stephen M. Schmitt and David A. Chance, *The Journal of Prosthetic Dentistry*, Vol 73, No 3 (March 1995) pp 280–283, and "Fabrication of Titanium Implant-Retained Restorations With Nontraditional Machining Techniques," by Steven M. Schmitt and David A. Chance, *The International Journal of Prosthodontics*, Vol 8, No 4 (1995), pp 332–336, and *Modern Practice In Orthognathic And Reconstructive Surgery*, Volume 1, William H. Bell, Ed, Part 7, "Analytical Model Surgery," the teachings of all of which articles are incorporated by reference herein.

Figure 1:
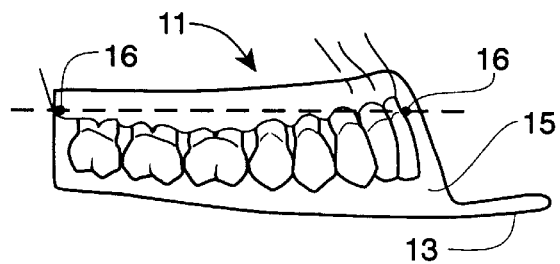
FIG. 1 illustrates the acquisition of an impression of the teeth, gums and palate of a patient using an impression tray and impression material.
Figure 2:
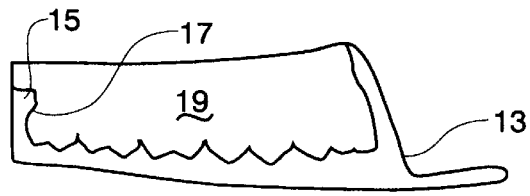
FIG. 2 illustrates the impression acquired according to FIG. 1.

Referring now to the drawings, FIGS. 1–6 illustrate generally the process for acquiring data defining the dental anatomy of a patient in the process for fabricating a dental device according to the invention. As suggested in FIG. 1, an impression of the patient's teeth, gums, palate and soft tissues 11 may be made in the conventional way using impression tray 13 containing conventional impression material 15 such as vinyl polysiloxane, polyether, polysulfide rubber and hydrocolloid. As shown in FIG. 2, removal of impression tray 13 from the patient's mouth results in a cavity 17 in the material 15 which accurately defines the shape of the teeth and soft tissues 11 of the patient. Cavity 17 is then filled with a material 19 distinguishable from material 15, such as different in composition, color or shade of color. It is noted that only the upper teeth and soft tissues of the patient are illustrated in FIGS. 1–6, although substantially the same procedures may be followed to make an impression of the lower teeth. An impression of both the upper and lower teeth taken at the same time (commonly referred to as a triple tray impression) contains information both about the teeth in one arch and about the positional relationship of one jaw to the other. If one color impression material is used to make the impression and two other different colors are used to fill the cavity defining the shape of the upper and lower teeth and tissues respectively, precise positional data about each arch and their anatomic spatial relationship can be obtained.

Figure 3:
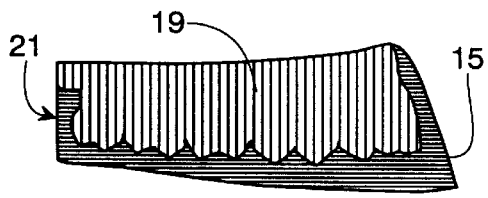
FIG. 3 is a sectional view of the hardened block of impression material following acquisition of the impression according to FIGS. 1 and 2.
Figure 4:
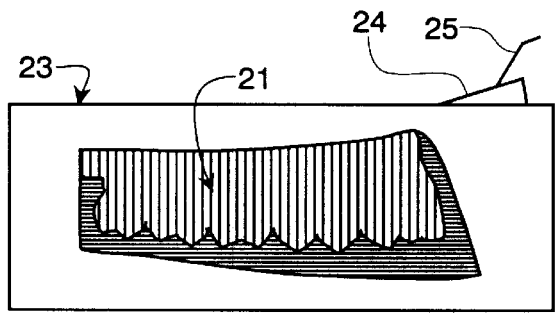
FIG. 4 illustrates the use of a microtome for slicing the hardened block of FIG. 3 according to the method of the invention.
Figure 5:
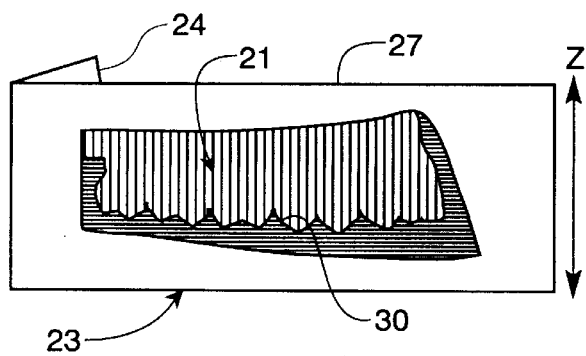
FIG. 5 illustrates the removal of a microtome slice according to FIG. 4.

Referring now to FIG. 3, shown therein is a sectional view of hardened block 21 comprising a composite of impression material 15 and of second impression material 19. As suggested in FIG. 4, block 21 is placed in a microtome 23 having blade 24 for slicing very thin uniform layers (slice 25) from block 21. After each slice 25 of material is removed the then remaining thickness of block 21 is noted. Slices 25 of thicknesses in the range of about 0.1 to 0.001 mm are normally taken in the process of the invention. The surface 27 (FIG. 5) remaining after each slice 25 is removed is then imaged, as suggested in FIG. 6, with a high resolution flat bed scanner 28, solid state charge-couple device (CCD) camera 29 or other suitable imaging device to produce a high resolution image of the contour of impression material 19 corresponding to the contour of the teeth and soft tissue 11 of the patient. If color scanning is used, precise data about each separate color of impression material 15,19 can be obtained. It is noted that other layer removal (slicing, milling or machining) methods may be used by one skilled in the art guided by these teachings to obtain contour images at known depths into block 21, the specific method not considered limiting of these teachings or the appended claims.

Alternatively, a conventional dental cast (not shown) may be obtained and placed into dental stone of different color or value. Thin layers of the surface may then be successively removed as by milling and the surfaces imaged, in manner as with the impression material, after each layer is removed. This alternative does require the construction of a dental cast, but is useful for some diagnostic processes.

Referring again to FIG. 1, it is further noted that radiopaque markers used to position a patient for CT or MRI scanning may be used in the practice of the invention for facilitating the slicing and imaging process of the invention and for supplementing data obtained by CT or MRI scanning. CT or MRI imaging is obtained by positioning the patient's head such that the slices of the CT/MRI scanner are parallel with the radiographic markers. Scatter from dental restorations is projected away from the diagnostic areas of the osseous anatomy. Data for the teeth and soft tissues may be obtained using the invention and combined with the CT/MRI data to produce an accurate CAD model of the teeth, soft tissues and osseous structures with minimal radiographic scatter. The markers may be luted to a dental cast in positions identical to those for the CT/MRI scan and the cast sliced (parallel to the plane of the markers) and imaged as described herein to provide data which may be combined with the CT/MRI data to define a three-dimensional model of the teeth and tissues and to program a numerically controlled (N/C) milling machine. For example, the codes from the slice data may define indentations for the teeth in a piece of plastic which may be used during surgery to properly position the jaws after they have been separated from the skull or the condylar aspect of the mandible.

The imaging data obtained in accordance with the invention as just is described is processed using conventional tracing programs to record contour 37 of the junction of the two (or several) different colors of impression materials. Once processed, contour 30 can be converted to a two-dimensional CAD file format such as DXF (AutoDesk Co). Because each slice is of known thickness, a contour map of the topography of the tissues can be made. Slices 25 can then be used to build a computer model of the teeth and tissues 11 displayed as a wire-frame, surface or solid CAD object. Anatomy from one side of the arch or face can be mirrored in the CAD program to produce symmetrical aesthetic dental restorations for missing tissues and teeth on the other side of the mouth or face. The 3D models can be converted to stereolithography (.stl) files to produce castable patterns. The models may be used to machine a restoration representing any selected portion of the model. This same data can also be used to control the milling of copper or graphite to create negative electrodes to refine and machine computer generated castings for precise fit or to machine a blank of metal using EDM such as taught in co-pending application Ser. No. 08/581,795 by Schmitt et al, entitled "Method of Fabricating Precise Cast or Noncast Implant Retained Dental Restorations Using Electrical Discharge Machines," the entire teachings of which are incorporated by reference herein. Because the electrode wears at the same time the workpiece (dental device) is being machined, the electrode contour changes and inaccuracies can occur. In accordance with the teachings of the invention, these inaccuracies can be corrected by remilling the same electrode and increasing the Z axis dimension to resurface the electrode.

Referring now to FIG. 7a, shown therein is a typical image 35 of a sliced surface 27 of impression block 21 after removal of a slice 25 or after milling of surface 27 in the process suggested above in relation to FIG. 6. The resolution or precision of scanner 28 or CCD camera 29 can produce micron level images 35 of sliced block 21. The information is two-dimensional and is saved as pixels defining the color and value of the surface 27. This data can be transformed into any number of file formats that can be used in CAD or CAM systems, including, but not necessarily limited to, ProE, Imagware or Mimics (Cad Key Inc., 4 Griffin Road North, Winsor Conn; Auto Cad release 13. Auto Desk Co.; Pro Engineer, Fast Surf, 6 South Washington St Suite 14, Sonora Calif.). As shown in FIG. 7b, image 35 can be converted to points that define contour 37 between the two impression materials, or the image of surface 27 can be transformed into a polyline image, and described as a spline. Referring now to FIG. 8, shown therein is a two-dimensional display of a series 39 of contours 37 of FIG. 7 defined by the corresponding series of images 35 taken at successive known positions (along the z direction of FIG. 6) within block 21 following successive removal of a plurality of slices 25. The data is converted to multiple DXF (AutoDesk Co) format polyline files, each corresponding to a specific z dimension. Using data defining series 39 of contours 37, three-dimensional CAD parts may be fabricated.

Figure 10:
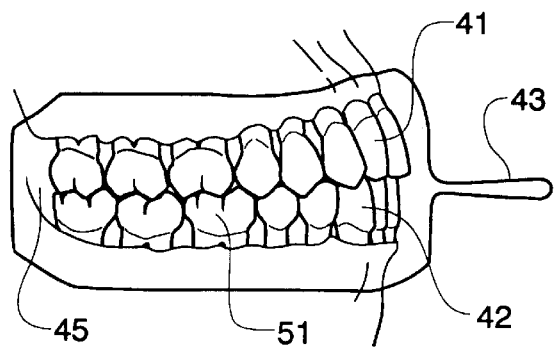
Figure 11:
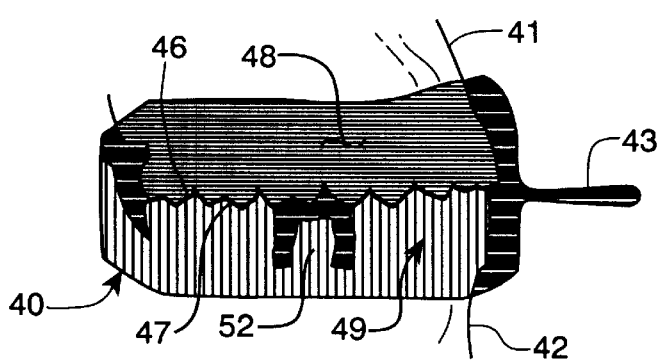
Figure 12:
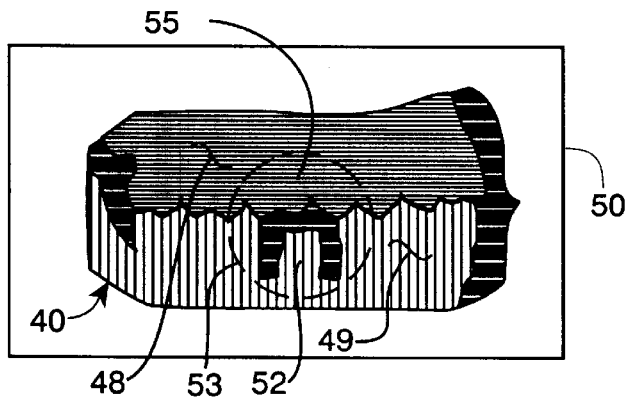
Figure 13A:
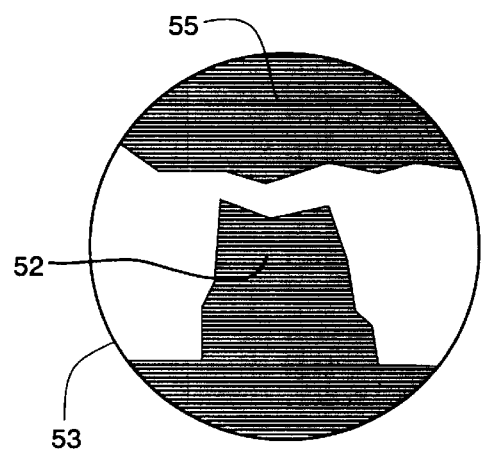
FIGS. 13a,b show a portion of the impression of FIGS. 9–12 including the contour of a tooth for which a restoration is desired as part of the imaging process of the invention.
Figure 13B:
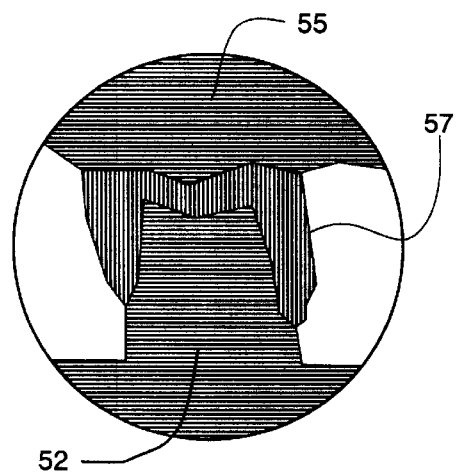
Figure 14:
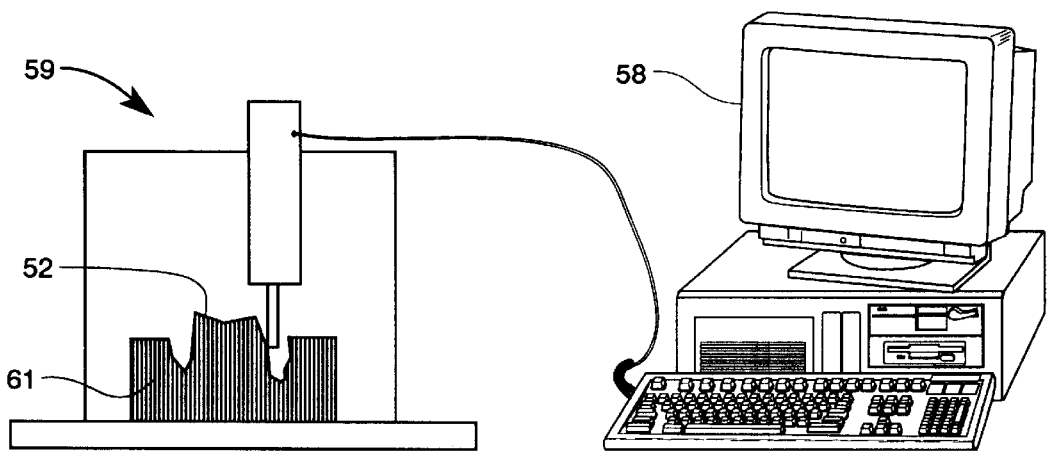
FIG. 14 illustrates the process of milling an electrode for use in the EDM process for fabricating the desired restoration defined in relation to FIGS. 13a,b.

Referring now to FIGS. 9–12, illustrated therein is a process similar to that just described, but for generating an impression 40 of both the upper teeth 41 and lower teeth 42, and for forming a microtome block for slicing and imaging. A triple tray 43 impression of both the upper teeth 41 and lower teeth 42 is taken in conventional fashion using impression material 45 (FIG. 10). Cavities 46, 47 defining the respective impressions of the upper teeth 41 and lower teeth 42 are then filled with impression materials 48,49 of color or shade different from that of material 45 (FIG. 11). The composite casting microtome block 50 (FIG. 12) enclosing impression 40 defined by impression materials 45,48,49 is then processed as suggested above for block 21 in association with the successive slicing and imaging process of FIGS. 4–6. In FIGS. 10–12 it is noted that a lower tooth 51 may require restoration in the form of a cap, crown or implant. In FIGS. 11,12, the impression of tooth 51 is shown at 52. FIG. 13a shows a somewhat enlarged view of that portion 53 of impression 40 including impression 52 of lower tooth 51 and that portion 55 of the upper teeth 41 which should be matched in fabricating a restoration for tooth 51. The contour data generated by the successive slicing and imaging of microtome block 50 (in manner similar to that described above in relation to FIGS. 4–6) precisely defines the contour 52 of tooth 51 and the contour 55 of the mating upper teeth. The precise shape of the cap or crown 57 is therefore defined between the contours 52,55. With reference now to FIG. 14, the slice and image data defining the contours of impression 52, portion 55 and crown 57 (FIGS. 11,12,13a,b) may according to the teachings hereof be utilized to create electrodes from graphite, copper, copper/graphite or brass with a computer 58 operated N/C milling machine 59 or other suitable means using pocketing and contouring routines. The codes from the slice and image data cut the indentations for the restoration in the electrode 61 material and electrode 61 is then used to machine the desired dental restoration using EDM. The electrode 61 wears as the EDM process proceeds, but can be resurfaced at a new value for z (see e.g., FIGS. 5,6) on the N/C machine and the EDM process continued. Electrode 61 may also be used to create the restoration from an uncast ingot of metal although at a somewhat longer machining period.

Figure 15:
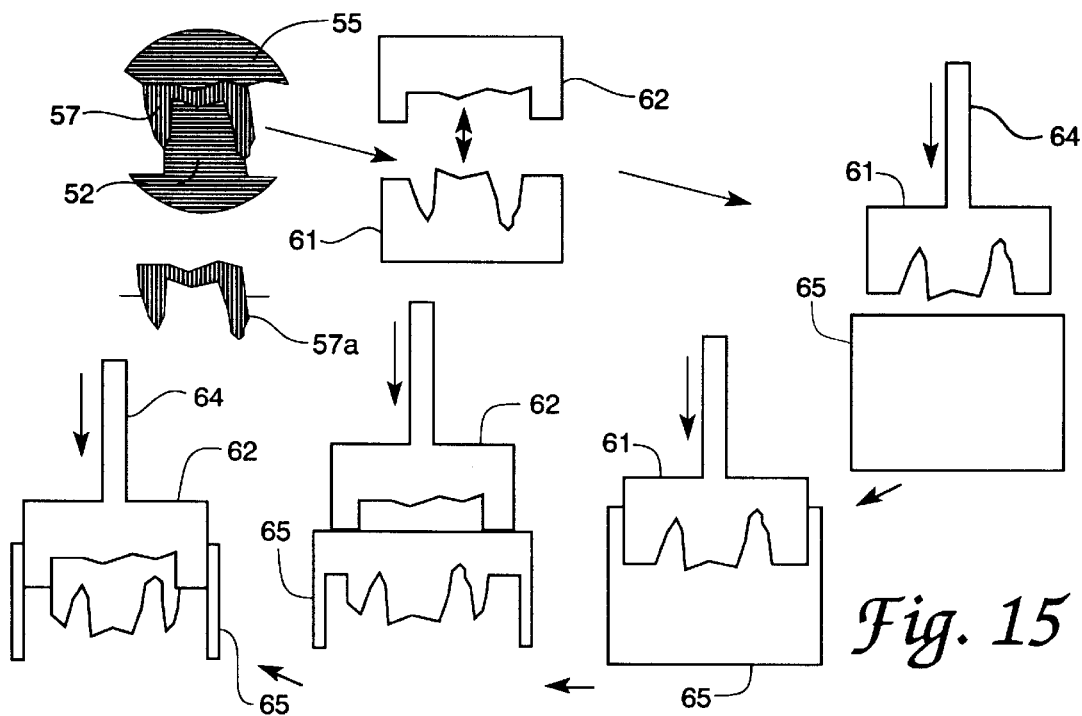
FIG. 15 illustrates the process according to the invention for fabricating a restoration from an uncast ingot of metal.

Referring now to FIG. 15, illustrated therein is the process according to the invention for fabricating a restoration (exemplified by crown impression 57) from an uncast ingot of metal. Using the data defining the contours of impression 52,55 and of crown 57, electrodes 61,62 are machined according to the procedure described above in relation to FIG. 14. The electrodes 61,62 are placed in an EDM machine 64 around an ingot 65 of metal which is then machined by EDM to the shape of the completed crown 57a.

Figure 16:
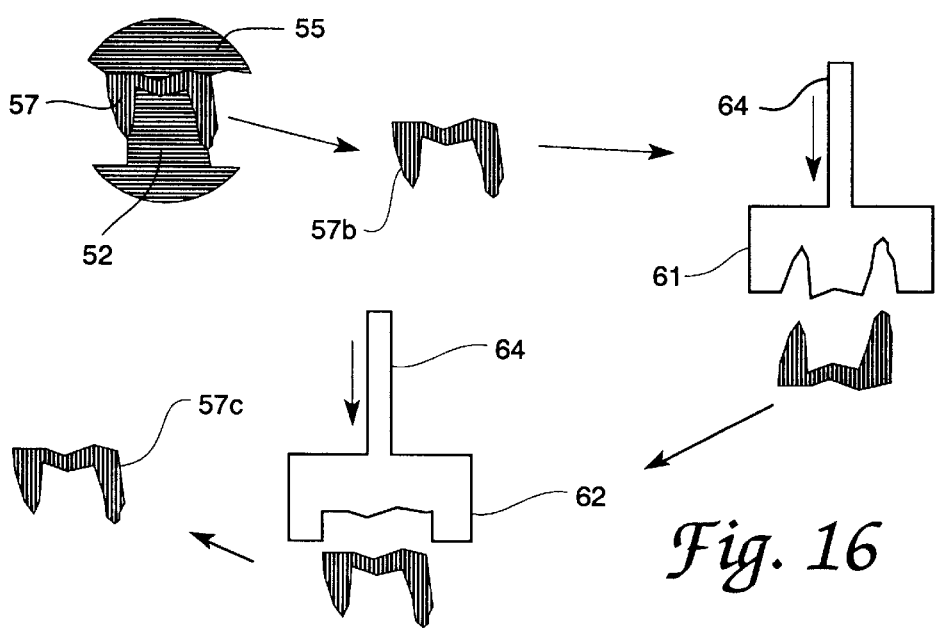
FIG. 16 illustrates the process according to the invention for fabricating a restoration from a cast ingot of metal.

Referring now to FIG. 16, illustrated therein is the process according to the invention for fabricating a restoration from a cast ingot of metal. The contour data derived above for defining the shape of crown impression 57 may be used to produce an .stl file for rapid prototyping a cast pattern 57b to near net shape. Cast pattern 57b may then be placed between electrodes 61,62 for finish EDM machining to the precise shape desired for completed restoration (crown) 57c.

Figure 17:
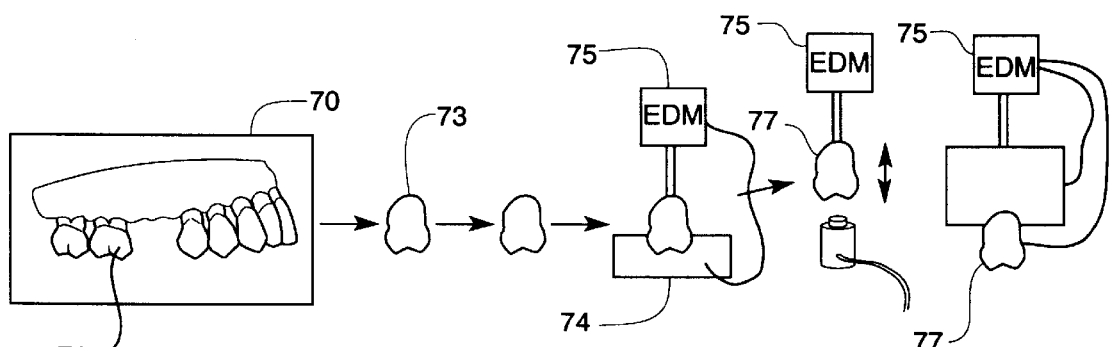
FIG. 17 illustrates the process according to the invention for fabricating a cast implant retained restoration.

Referring now to FIG. 17, illustrated therein is the process according to the invention for fabricating a cast implant retained restoration. A microtome block 70 containing an impression 71 of impression material or dental stone is processed by successive slicing and imaging as described above in order to create an .stl file defining the contour of the missing tooth and to construct the restoration as a mirror image of the adjoining front tooth and to join the restoration to an implant head (not shown). A pattern 73 of the missing tooth is made using a rapid prototyping process. A cast pattern in gold, gold alloy or titanium is made according to the processes just described in relation to FIGS. 15,16 and data from the imaging process is used to N/C mill a negative electrode of the tissue surface of the tooth in graphite, copper or copper/graphite by EDM 75. The internal aspect of the casting is then fitted to a copper, brass or graphite analog of the implant 77. Electrode 74 is then EDM machined using the slice imaging data fitting the occlusal and incisal surfaces.

This process has the advantage that it does not use radiation and the scatter seen in CT is eliminated. Since CT and MRI data can be represented as 3D CAD models, information obtained in the practice of the invention may be combined with CT and MRI data to produce precise anatomic models for diagnosis and treatment of patients with skeletal and dental deformities.

The invention therefore provides a method for imaging small objects in the custom fabrication of machined dental devices. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. A method for fabricating a dental restoration for a patient, comprising the steps of:
   (a) providing a dental impression tray containing a first impression material;
   (b) obtaining a dental impression of a patient using said impression tray and first impression material, said dental impression defining a cavity in said first impression material corresponding to the shape of the teeth, gums and palate of the patient;
   (c) filling said cavity with a second material distinguishable from said first material and allowing said first and second materials to harden to a solid block of said first and second material;
   (d) successively removing from said block thin uniform layers of predetermined known thickness of said first and second material and imaging the then remaining surface of said block after each successive layer is removed to define a contour of said second material for each said layer removed, each said contour defining the contour of the teeth, gums and palate of the patient at a corresponding known depth of removal from said block of said successive layers;
   (e) generating a three dimensional computer model of the teeth, gums and palate of the patient using said contours and said corresponding known depths of removal of said successive layers; and
   (f) machining a restoration corresponding to said three dimensional computer model.

2. The method of claim 1 wherein said first impression material is selected from the group consisting of vinyl polysiloxane, polyether, polysulfide rubber and hydrocolloid.

3. The method of claim 2 wherein said first and second materials are the same material of different respective colors or shades of color.

4. The method of claim 1 wherein said layers are removed in a thickness range of about 0.001 to 0.1 mm.

5. The method of claim 1 wherein the step of removing said layers from said block is performed in a microtome.

6. The method of claim 1 wherein the step of imaging each said then remaining surface is performed using a high resolution flat bed scanner or a solid state charge-couple device camera.

7. The method of claim 1 further comprising the step of converting said three dimensional computer model to a stereolithography file for producing a castable pattern of said model.

8. A method for fabricating a dental restoration for a patient, comprising the steps of:
   (a) providing dental impression trays for obtaining impressions of the upper and lower teeth and gums of a patient, each said tray containing a dental impression material of a first color;
   (b) obtaining upper and lower dental impressions of the patient using said impression trays and said dental impression material, said dental impressions defining first and second cavities in said dental impression material corresponding respectively to the shape of the upper teeth, gums and palate and to the shape of the lower teeth and gums of the patient;
   (c) filling said first cavity with said dental impression material of second color different from said first color, and filling said second cavity with said dental impression material of third color different from said first and second colors, and allowing said dental material to harden to a solid block;
   (d) successively removing from said block thin uniform layers of predetermined known thickness and imaging the then remaining surface of said block after each successive layer is removed to define contours of said dental material of said second and third colors for each said layer removed;
   (e) generating a three dimensional computer model of the teeth, gums and palate of the patient using said contours; and
   (f) machining a restoration corresponding to a selected portion of said three dimensional computer model.

9. The method of claim 8 wherein said dental impression material is selected from the group consisting of vinyl polysiloxane, polyether, polysulfide rubber and hydrocolloid.

10. The method of claim 8 wherein said layers are removed in a thickness range of about 0.001 to 0.1 mm.

11. The method of claim 8 wherein the step of slicing said block of first and second material is performed in a microtome.

12. The method of claim 8 wherein the step of imaging each said then remaining surface is performed using a high resolution flat bed scanner or a solid state charge-couple device camera.

13. The method of claim 8 further comprising the step of converting said three dimensional computer model to a stereolithography file for producing a castable pattern of said model.

* * * * *